(12) United States Patent
Saito et al.

(10) Patent No.: US 8,465,933 B2
(45) Date of Patent: Jun. 18, 2013

(54) METHOD FOR SCREENING HUMAN ABO BLOOD GROUP-BINDING LACTOBACILLI

(75) Inventors: Tadao Saito, Miyagi (JP); Yasushi Kawai, Miyagi (JP); Hideaki Uchida, Miyagi (JP); Katsunori Kimura, Kanagawa (JP); Kakuhei Isawa, Kanagawa (JP); Keisuke Furuichi, Kanagawa (JP)

(73) Assignee: Meiji Co., Ltd, Tokyo (JP)

( * ) Notice: Subject to any disclaimer, the term of this patent is extended or adjusted under 35 U.S.C. 154(b) by 234 days.

(21) Appl. No.: 12/987,518

(22) Filed: Jan. 10, 2011

(65) Prior Publication Data

US 2011/0104721 A1    May 5, 2011

Related U.S. Application Data

(62) Division of application No. 11/720,462, filed as application No. PCT/JP2005/022096 on Dec. 1, 2005, now Pat. No. 7,897,374.

(30) Foreign Application Priority Data

Dec. 1, 2004   (JP) .................................. 2004-349135
Jun. 16, 2005  (WO) .................. PCT/JP2005/011043

(51) Int. Cl.
    *G01N 33/53*   (2006.01)
(52) U.S. Cl.
    USPC ........... 435/7.1; 435/34; 435/252.9; 424/93.4
(58) Field of Classification Search
    None
    See application file for complete search history.

(56) References Cited

U.S. PATENT DOCUMENTS 6,596,530 B1    7/2003  Kimura et al.
2005/0163888 A1 7/2005  Hayashi et al.

FOREIGN PATENT DOCUMENTS

JP      2004-101249 A    4/2004

OTHER PUBLICATIONS

Garcher C. et al., Expression of mucin peptide and blood group ABH- and Lewis-related carbohydrate antigens in normal human conjunctiva, Invest. Ophthalmol. Vis. Sci., Mar. 1994, vol. 35, No. 3, pp. 1184-1191.*
Etzioni R. et al., Combining biomarkers to detect disease with application to prostate cancer, Biostatistics, 2003, vol. 4, No. 4, pp. 523-538.*
Hoskins L.C. et al., Degradation of blood group antigens in human colon ecosystem, The Journal of Clinical Investigation, Jan. 1976, vol. 57, pp. 74-82.*
Saito et al., "The production of a new selection system for probiotic lactic acid bacteria adhering to animal intestines and its application," *Research Report for Grants-in-Aid for Scientific Research (B) (2)*, 2002, pp. 86-117, H12-13.
Amano, "Structures of blood-group sugar chains on gastrointestinal tract mucin: toward elucidation of the mechanism of bacterial infection," *Seikagaku*, Apr. 1999, vol. 71, No. 4, pp. 274-277.

Fratamico et al, "Detection of *Escherichia coli* 0157:H7 using a surface plasmon resonance biosensor," *Biotechnology Techniques*, Jul. 1998, vol. 12, No. 7, pp. 571-576.
Holgersson et al., "Glycolipids of human large intestine: difference in glycolipid expression related to anatomical localization, epithelial/non-epithelial tissue and the *ABO, Le*, and *Se* phenotypes of the donors," *Biochimie*, Nov. 1988, vol. 70, No. 11, pp. 1565-1574.
Holgersson et al, "Glycosphingolipids of Human Large Intestine: Detailed Structural Characterization with Special Reference to Blood Group Compounds and Bacterial Receptor Structures," *J. Biochem.*, Jul. 1991, vol. 110, No. 1, pp. 120-131.
Holmes et al., "Studies on the interaction of *Staphylococcus aureus* and *Staphylococcus epidermidis* with fibronectin using surface plasmon resonance (BIAcore)," *Journal of Microbiological Methods*, 1997, vol. 28, No. 1, pp. 77-84.
Matsumura et al. New binding assay and preparative trial of cell-surface lectin from *Lactobacillus acidophilus* group lactic acid bacteria, *Journal of Dairy Science*, 1999, pp. 2525-2529, vol. 82, No. 12.
Saito, Heisei 15 Nendo Kenkyu no Galyo (2003), The Food Science Institute Foundation, Jun. 2004, vol. 16, pp. 1-7.
Saito, "A new selection system for human intestinal tract adherent lactic acid bacteria and development of new functional yogurt," *Bioscience and Industry*, 2004, vol. 62, No. 11, pp. 728-731.
Saito et al., "A New Screening Method for Probiotic Lactic Acid Bacteria in the *Lactobacillus acidophilus* Group by Using Carbohydrate Probes," *Anim. Sci. J.*, 2000, vol. 71, No. 1, pp. 103-108.
Saito, T. Selection of useful probiotic lactic acid bacteria from the *Lactobacillus acidophilus* group and their applications to functional foods, Review Article, *Animal Science Journal*, Jan. 2004, pp. 1-13, vol. 75, No. 1.
Sudha et al., "Adherence of *Shigella dysenteriae* 1 to Human Colonic Mucin," *Current Microbiology*, Jun. 2001, vol. 42, No. 6, pp. 381-387.
Takahashi et al, "A New Screening Method for the Selection of *Lactobacillus acidophilus* Group Lactic Acid Bacteria with High Adhesion to Human Colonic Mucosa," *Biosci. Biotechnol. Biochem.*, Sep. 1996, vol. 60, No. 9, pp. 1434-1438.
Uchida et al., "A New Assay Using Surface Plasmon Resonance (SPR) to Determine Binding of the *Lactobacillus acidophilus* Group to Human Colonic Mucin," *Biosci. Biotechnol. Biochem.*, May 2004, vol. 68, No. 5, pp. 1004-1010.
Uchida et al., Jpn. J. Lactic Acid Bact., Jun. 2004, vol. 15, No. 1, p. 35, #16.
Vaňák et al., "Využití Monoklonálních Protilátek K Detekci Antigenů Krevních Skupin A A B Ve Sliznici Tlustého Střeva," *Čas Lék Česk.*, Mar. 1988, vol. 127, No. 12, pp. 364-367.

* cited by examiner

*Primary Examiner* — Jon P Weber
*Assistant Examiner* — Satyendra Singh
(74) *Attorney, Agent, or Firm* — Saliwanchik, Lloyd & Eisenschenk

(57) ABSTRACT

*Lactobacillus* screening methods were carried out using surface plasmon resonance spectrums and human intestinal mucin and blood group antigens as probes. A trial to set selection criteria in the above-mentioned methods of screening for lactobacilli was made to adapt the methods to mass screening, and it was discovered that lactobacilli compatible with ABO blood groups can be screened by setting 100 RU as a criterion for judging bacterial binding under certain conditions. Using 238 *lactobacillus* strains, the above-mentioned screening methods and tests to judge their compatibility for the use of yogurt production were carried out, to at long last specifically discover *bacillus* strains compatible with blood groups A, B, and O.

9 Claims, 2 Drawing Sheets

SUGAR CHAIN REGION OF BLOOD
GROUP A SUGAR CHAIN BP PROBE

A ANTIGEN

SUGAR CHAIN REGION OF BLOOD
GROUP B SUGAR CHAIN BP PROBE

B ANTIGEN

INDICATING SUGARS IN THE ANTIGEN'S EPITOPE REGION

SUGAR CHAIN REGION OF BLOOD
GROUP O SUGAR CHAIN BP PROBE

H ANTIGEN

METHOD FOR SCREENING HUMAN ABO BLOOD GROUP-BINDING LACTOBACILLI

CROSS-REFERENCE TO RELATED APPLICATIONS

This application is a divisional application of U.S. Ser. No. 11/720,462, filed Aug. 24, 2007, now U.S. Pat. No. 7,897,374; which is a National Stage Application of International Application Number PCT/JP2005/022096, filed Dec. 1, 2005; which claims priority to JP 2004-349135, filed Dec. 1, 2004 and also claims priority to International Application Number PCT/JP2005/011043, filed Jun. 16, 2005; all of which are incorporated herein by reference in their entireties.

TECHNICAL FIELD

The present invention relates to lactobacilli and screening of lactobacilli.

BACKGROUND ART

About 200 species, 100 trillion ($10^{14}$) or more intestinal bacteria (intestine-colonizing microorganisms) inhabit the human intestine. Microorganisms called probiotics improve the intestinal balance between useful and harmful bacteria, contributing to host health. Recently, a trend is to apply these probiotic microorganisms to foods. For example, several kinds of functional yogurt produced using lactobacilli with probiotic functions have been commercialized. Thus, a mass screening technique for selecting more excellent probiotics is required.

Intestine-colonizing lactobacilli propagate while adhering to the human intestine. Thus, the property of lactobacilli to bind to the intestine is very important for the exertion of probiotic functions. The binding mechanism of lactobacilli in the human intestine is not yet elucidated. Prior studies on intestinal lactobacilli have confirmed that *Lactobacillus casei* has the ability to bind to sugar chains of glycolipids and that *L. reuteri* and *L. crispatus* have a collagen-binding ability. In addition, lectin-like proteins which bind to the above-mentioned intestinal lactobacilli have been identified. However, cytoskeleton protein (collagen)-exposed areas are very few in the intestinal epithelia of most healthy individuals, and colonization of lactobacilli via lectin-like proteins in the intestinal epithelia is unlikely. Thus, sugar chains that bind to intestinal mucin are considered to play an important role in ability of intestine-colonizing lactobacilli to bind to the intestine. Surface layer proteins (SLPs) of many intestine-colonizing lactobacilli have lectin-like proteins, which are sugar-recognizing proteins. Intestinal mucin exists on intestinal surface.

Intestinal mucin is a mucous high-molecular-weight glycoprotein having countless mucin-type sugar chains linked to a polypeptide (a core protein, apomucin) via O-glycosidic linkages. In sum, intestine-colonizing lactobacilli are considered to acquire intestine-binding ability by binding to sugar chains of intestinal mucin through lectin-like proteins on their surface and establishing a stable growth.

Meanwhile, an interesting fact that has recently been reported is that the chemical structure of sugar chains constituting human colonic mucin (HCM) varies depending on the ABO blood group (Non-Patent Documents 1 to 4).

Human ABO blood groups are distinguished depending on the type of antigenic substance expressed on red blood cell surface. The antigenic sites of these ABO blood group substances are sugar chains of certain chemical structures (ABO blood group antigens). Both blood group A- and B-antigens are molecules consisting of three sugars. The blood group A-antigen is a molecule in which an α-N-acetylgalactosamine is bound to a basic structure called blood group H antigen that consists of two sugars through a specific linkage mode, whereas the blood group B antigen is a molecule in which α-galactose is bound. Humans of blood group A, blood group B, and blood group AB express A antigen, B antigen, and both A and B antigens on the surface of red blood cells, respectively. In contrast, humans of blood group O express H antigen, which is the basic structure.

The above scientific fact that the sugar chain structure of digestive-tract mucin varies blood group-dependently suggests that the type of probiotic lactobacilli that bind to and grow in the digestive tract varies depending on the blood group. Development of functional yogurt tailored at individual levels will be made possible if lactobacilli that are compatible with each blood group are found. Focusing on this point, the present inventors have hitherto developed a method of screening for human intestine-binding lactobacilli using their adsorbability to ABO blood group antigens (Patent Document 1). This is an epoch-making method that detects adsorbability of lactobacilli to ABO blood group antigens by using surface plasmon resonance (SPR) spectrums, and thereby selecting compatible lactobacilli according to blood groups. Specifically, by using ABO blood group antigens or intestine-derived mucin as ligands, the method detects the binding between lactobacilli and the ligands occurring when the lactobacilli are contacted with the ligands immobilized on a sensor chip, through detecting a mass change on the sensor chip which accompanies the binding as a surface plasmon resonance (SPR) signal. The above-mentioned mass change is expressed by resonance units (RU). One RU equals 1 $pg/mm^2$, and means that 1 pg of a substance is bound per 1 $mm^2$. The present inventors carried out the above method, and confirmed that *Lactobacillus crispatus* JCM8778 strain and *Lactobacillus acidophilus* OLL2769 strain recognize blood group A antigen (Patent Document 1 and Non-Patent Document 5). However, an increased demand for foods that use probiotic lactobacilli including yogurt is expected, and thus acquisition of lactobacilli having blood group specific binding capabilities and with better binding properties has been awaited.

[Patent Document 1] Japanese Laid Open Patent Application No. 2004-101249 (unexamined, published Japanese patent application)

[Non-Patent Document 1] Junko Amano, Seikagaku, The Japanese Biochemical Society, 1999, Vol. 71, p. 274-277

[Non-Patent Document 2] Holgersson, J., Stromberg, N., and Breimer, M. E., Glycolipids of human large intestine: glycolopid expression related to anatomical localization, epithelial/non-epithelial tissue and the ABO, Le and Se phenotypes of the donors. Biochimie, 70, 1565-1574 (1988).

[Non-Patent Document 3] Holgersson, J., Jovall, P. A., and Breimer, M. E., Glycosphingolipids of human large intestine: detailed structural characterization with special reference to blood group compounds and bacterial receptor structures. J. Biochem, (Tokyo), 110, 120-131 (1991).

[Non-Patent Document 4] Vanak, J., Ehrmann, J., Drimalova, D., Nemec, M., monoclonal antibodies in the detection of blood group antigens A and B in the mucosa of the large intestine. Cas Lek Cesk, 18, 364-367 (1988).

[Non-Patent Document 5] Uchida, H. et al., Biosci. Biotechnol. Biochem., 68(5), 1004-1010 (2004).

[Non-Patent Document 6] Holmes, S. D. et al., Studies on the interaction of *Staphylococcus aureus* and *Staphylococcus*

*epidermidis* with fibronectin using surface plasmon resonance (BIACORE)., J. Microbiological Methods, 28, 77-84 (1997).

[Non-Patent Document 7] Fratamico, P. M. et al., Detection of *Escherichia coli* O157:H7 using a surface plasmon resonance biosensor. Biotechnol. Techniques. 7, 571-576 (1998).

DISCLOSURE OF THE INVENTION

Problems to be Solved by the Invention

The present invention was achieved in view of the above circumstances. A problem to be solved by the present invention is to discover novel intestine-binding lactobacilli compatible with human ABO-blood groups.

Means for Solving the Problems

To solve the above-mentioned problems, the present inventors carried out the above-mentioned lactobacilli screening method that utilizes surface plasmon resonance spectrums. The above-mentioned method has already been established as a screening method for lactobacilli, but the present inventors set "selection criteria values" in the above-mentioned screening method for lactobacilli in order to make the method more adaptable to mass screening. Examples of prior studies on bacteria using surface plasmon resonance spectrums, are where binding between *Staphylococcus aureus* and fibronectin was measured by using surface plasmon resonance spectrums (Non-Patent Document 6) and where *Escherichia coli* O157 was detected by using protein A or protein G immobilized on a chip via anti-*Escherichia coli* O157 antibodies (Non-Patent Document 7). The RU values indicating binding of live bacteria were from about 100 to 1,000 RU in these studies. However, no example of an investigation of lactobacilli using surface plasmon resonance spectrums was known except for the reports by the present inventors (Patent Document 1 and Non-Patent Document 5). Furthermore, RU values could vary depending on various measurement conditions even if test samples were the same. Thus, the present inventors conducted dedicated research, and as a result, established screening methods for ABO blood group-compatible lactobacilli, by setting 100 RU as a criterion under certain conditions.

Moreover, the present inventors carried out the above-mentioned screening methods on 238 separate human intestine-derived *lactobacillus* strains isolated from human intestine, further conducted tests to judge their suitability for use in yogurt production, and at long last specifically discovered *bacillus* strains compatible with blood groups A, B and O. Namely, the present invention relates to lactobacilli suitable for blood group-compatible yogurt and screening methods for the lactobacilli, and specifically provides the following inventions:

[1] An intestine-binding *lactobacillus Lactobacillus gasseri*, having the ability to bind to a human ABO blood group antigen represented by any one of the following formulas of:
   (a) [GalNAcα1-3(Fucα1-2)Gal-];
   (b) [Galα1-3(Fucα1-2)Gal-]; and
   (c) [Fucα1-2Gal-].
[2] The *lactobacillus Lactobacillus gasseri* of [1], wherein the *lactobacillus* is specified by any one of Accession No.: NITE BP-25, Accession No.: NITE BP-26, Accession No.: NITE BP-27, Accession No.: NITE BP-28, Accession No.: NITE BP-145, and Accession No.: NITE BP-146.

[3] A starter for producing a human ABO blood group-compatible fermented milk and dairy product, comprising the *lactobacillus Lactobacillus gasseri* of [1] or [2].
[4] A food and drink product, comprising the *lactobacillus Lactobacillus gasseri* of [1] or [2].
[5] A fermented milk and lactic acid bacteria beverage, comprising the *lactobacillus Lactobacillus gasseri* of [1] or [2].
[6] A method of screening for a *lactobacillus* using a surface plasmon resonance spectrum, wherein fulfillment of the following conditions (i) to (iii) is used as an index:
   (i) RU value indicating ability to bind to a human ABO blood group A antigen is 100 RU or higher;
   (ii) RU value indicating ability to bind to a human ABO blood group B and/or H antigen is 100 RU or lower; and
   (iii) RU value indicating ability to bind to human blood group A intestinal mucin is 100 RU or higher.
[7] A method of screening for a *lactobacillus* by using a surface plasmon resonance spectrum, wherein fulfillment of the following conditions is used as an index:
   (i) RU value indicating ability to bind to a human ABO blood group B antigen is 100 RU or higher;
   (ii) RU value indicating ability to bind to a human ABO blood group A and/or H antigen is 100 RU or lower; and
   (iii) RU value indicating ability to bind to human blood group B intestinal mucin is 100 RU or higher.
[8] A method of screening for a *lactobacillus* by using a surface plasmon resonance spectrum, wherein fulfillment of the following conditions is used as an index:
   (i) RU value indicating ability to bind to a human ABO blood group H antigen is 100 RU or higher;
   (ii) RU value indicating ability to bind to a human ABO blood group A and/or B antigen is 100 RU or lower; and
   (iii) RU value indicating ability to bind to human blood group O intestinal mucin is 100 RU or higher.
[9] A method of screening for a *lactobacillus* by using a surface plasmon resonance spectrum, wherein fulfillment of the following conditions is used as an index:
   (i) RU value indicating ability to bind to a human ABO blood group B antigen is 100 RU or higher;
   (ii) RU value indicating ability to bind to a human ABO blood group A and/or H antigen is 100 RU or lower; and
   (iii) RU value indicating ability to bind to human blood group B intestinal mucin is higher than an RU value indicating ability to bind to human blood group A intestinal mucin and an RU value indicating ability to bind to human blood group O intestinal mucin.

BEST MODE FOR CARRYING OUT THE INVENTION

Figure 1:
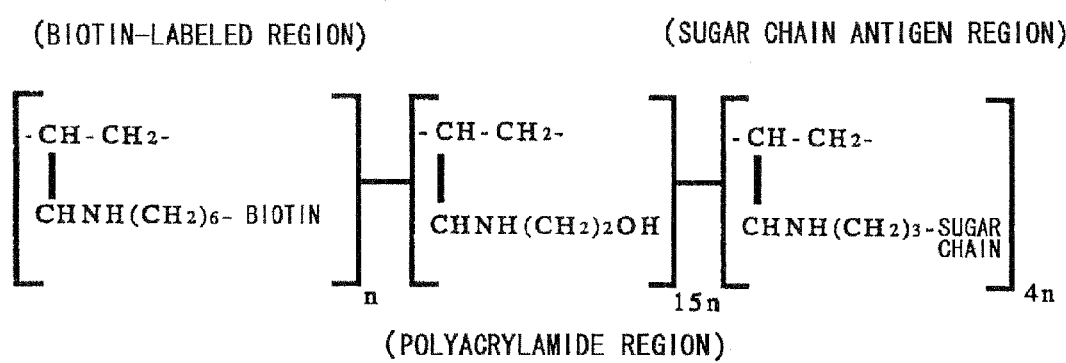
FIG. 1 is a drawing showing the chemical structure of biotinylated polymer (BP) probes that have sugar chain antigen regions of human ABO blood groups.

The present invention provides intestine-binding lactobacilli *Lactobacillus gasseri* having the ability to bind to human ABO blood group antigens that are represented by any one of the formulas of (a) [GalNAcα1-3(Fucα1-2)Gal-], (b) [Galα1-3(Fucα1-2)Gal-], and (c) [Fucα1-2Gal-].

"Lactobacilli" is generally a collective designation for a group of bacteria that produce lactic acid from glucose with a yield of 50% or more, when expressed by molar ratio conversion. Genus *Lactobacillus*, genus *Lactococcus*, genus *Streptococcus*, and genus *Leuconostoc* are representative genera of lactobacillus. Genus *Bifidobacterium* is also included in the lactobacillus of the present invention. Genus *Lactobacillus* is further classified into species. Representative bacteria species of genus *Lactobacillus* comprise *Lactobacillus delbruekii* subsp. *bulgaricus* (*L. bulgaricus*), *Lactobacillus delbruekii* subsp. *delbruekii* (*L. delbruekii*), lactobacilli of the group of *Lactobacillus acidophilus* (*L. acidophilus* group), *Lactobacillus casei* (*L. casei*), *Lactobacillus plantarum* (*L. plantarum*), *Lactobacillus brevis* (*L. brevis*), *Lactobacillus buchneri* (*L. buchneri*), *Lactobacillus fermentum* (*L. fermentum*), *Lactobacillus helveticus* (*L. helveticus*), and such. Depending on the results of DNA-DNA homology and cell wall component analysis, lactobacilli of *L. acidophilus* group are classified into six species: *Lactobacillus acidophilus* (A-1), *Lactobacillus crispatus* (A-2), *Lactobacillus amylovorus* (A-3), *Lactobacillus gallinarum* (A-4), *Lactobacillus gasseri* (B-1), and *Lactobacillus johnsonii* (B-2).

The lactobacilli *Lactobacillus gasseri* (herein below sometimes abbreviated as "*L. gasseri*") of the present invention are intestine-binding *Lactobacillus gasseri* characterized by the ability to bind to ABO blood group antigens. In the present invention, ABO blood group antigens refer to sugar chains that determine blood groups, and specifically, refer to blood group A sugar chain (A antigen): [GalNAcα1-3 (Fucα1-2) Gal-], blood group B sugar chain (B antigen): [Galα1-3 (Fucα1-2)Gal-], and blood group O sugar chain (refers to the sugar chain determining group O blood; also called H antigen or O antigen): [Fucα1-2Gal-]. As mentioned above, intestinal mucin present on intestinal surface have different sugar chains depending on the ABO blood group. Among lactobacilli that bind to mucin prepared from blood group A human intestine, the present inventors confirmed the existence of lactobacilli *L. gasseri* that bind to blood group A sugar chains, the antigen determining human blood group A. Further, the present inventors confirmed that blood group A sugar chains are expressed in the above-described mucin. Thus, the lactobacilli *L. gasseri* of the present invention that bind to the above-mentioned blood group A sugar chain, but which are not adsorbed onto sugar chains of other blood groups, bind to the blood group A sugar chains present on intestinal mucin, thereby acquiring intestine-binding ability in humans of the ABO blood group A. These lactobacilli *L. gasseri* are considered to stably bind to and proliferate in the intestine of blood group A individuals, leading to the exertion of probiotic functions. Namely, these lactobacilli *L. gasseri* can contribute to the health of, especially, blood group A individuals, and can be said to be compatible with blood group A individuals. Similarly, the lactobacilli *L. gasseri* of the present invention that bind to the above-mentioned blood group B sugar chain, but which are not adsorbed onto sugar chains of other blood groups, are compatible with ABO blood group B individuals. The lactobacilli *L. gasseri* of the present invention that bind to the above mentioned blood group O sugar chain, but which are not adsorbed onto sugar chains of other blood groups are compatible with ABO blood group O individuals.

The lactobacilli *L. gasseri* of the present invention (occasionally called below as "blood group-specifically-binding lactobacilli *L. gasseri*") can be isolated/separated from human feces. It is highly possible that lactobacilli *L. gasseri* compatible with blood group A individuals (abbreviated below as "group A-compatible lactobacilli") can be more efficiently isolated from feces of ABO blood group A individuals, lactobacilli *L. gasseri* compatible with blood group B individuals (abbreviated below as "group B-compatible lactobacilli") from feces of ABO blood group B individuals, and lactobacilli *L. gasseri* compatible with blood group O individuals (abbreviated below as "group O-compatible lactobacilli") from feces of ABO blood group O individuals. For isolation, properties of lactobacilli *L. gasseri* known to those skilled in the art can be used as indicators. For example, being bacillary, homofermenting, exhibiting aerobic growth, having no gas production, and such are usable as indicators.

Media generally suitable for culturing lactobacilli may be used for culturing the blood group-specifically-binding lactobacilli *L. gasseri* of the present invention, and media comprising carbon sources such as glucose, lactose, galactose, fructose, trehalose, sucrose, mannose, and cellobiose; nitrogen sources such as meat extracts, peptone, yeast extracts, casein, and whey proteins; and inorganic nutrients such as magnesium sulfate, ferrous sulfate, and manganese sulfate can be used. As one preferable example, Lactobacilli MRS broth (Difco, Ref No. 288130) can be given. The culture conditions are not especially restricted, as long as the growth of enteric lactobacilli is permitted. Preferable conditions include, for example, pH 5.0-pH 8.0 and temperature of 20° C.-45° C., and more preferable conditions are anaerobic, pH 5.0-pH7.0, and temperature of 30° C.-40° C.

One can know whether or not the *L. gasseri* isolated and cultured as mentioned above have blood group-specific binding ability to the intestine or binding ability to blood group antigens, by determining the presence or absence of their ability to bind to human intestinal mucin or blood group antigens. For example, bacterial surface layer proteins (SLPs) can be prepared from the surface of test bacteria, and the binding between SLPs labeled with biotin and such and intestinal mucin or blood group antigens can be detected. Alternatively, detection by the hybridization technique using labeled intestinal mucin or labeled blood group antigens after electrophoresis of the test bacteria's SLPs is also possible. Further, as in the later-mentioned Examples, the detection can be carried out with lactobacilli in a living state if a surface plasmon analytical apparatus (for example, BIACORE1000) is utilized.

To prepare human blood group-specific intestinal mucin, surface portions of human intestine of a certain blood group can be obtained, the portions subjected to gel filtration using a solubilizing agent such as guanidine hydrochloride, and then purified by using both a high absorbance of proteins and high content of neutral sugars as indicators. For instance, one can conduct such processes by referring to the method described in "Purushothaman, S. S. et al., Adherence of *Shigella dysenteriae* 1 to Human Colonic Mucin. Curr. Microbiol., 42(6), 381-387 (2001)." It is more preferable if the expression of blood group antigens in the prepared human intestinal mucin is confirmed by using anti-blood group antigen antibodies. The method described in Examples is given as a specific example. Meanwhile, with regard to blood group antigens, they may be synthesized based on the later-described formulas or sugar sequences described in FIG. 2, or use commercially available sugar chain probes (example: probes made by Seikagaku Corporation) or neoglycoprotein/blood group A-trisaccharide BSA (example: Calbiochem), neoglycoprotein/blood group B-trisaccharide BSA (example: Calbiochem), and such.

Representative blood group-specifically-binding lactobacilli *L. gasseri* of the present invention comprise *Lactobacillus gasseri* specified by any one of Accession No.: NITE BP-25, Accession No.: NITE BP-26, Accession No.: NITE BP-27, and Accession No.: NITE BP-28. Among them, the lactobacilli specified by Accession No.: NITE BP-26 and Accession No.: NITE BP-27 are group A-compatible lactobacilli, and those specified by Accession No.: NITE BP-25 and Accession No.: NITE BP-28 are group O-compatible lactobacilli. These bacterial strains are lactobacilli that were confirmed by the present inventors to be compatible with the above-mentioned each blood group. Further representative blood-group-specifically-binding lactobacilli *L. gasseri* of the present invention comprise *Lactobacillus gasseri* that are specified by Accession No.: NITE BP-145 or Accession No.: NITE BP-146. These lactobacilli specified by Accession No.: NITE BP-145 and Accession No.: NITE BP-146 are group B-compatible lactobacilli. These bacterial strains were confirmed by the present inventors to be compatible with blood group B.

The present inventors deposited these bacterial strains with the Patent Microorganisms Depositary (NPMD) of the National Institute of Technology and Evaluation according to the Budapest Treaty on the International Recognition of the Deposit of Microorganisms for the Purposes of Patent Procedure. Herein below, the contents specifying the deposit are described.

The contents for Accession Nos. NITE BP-25, 26, 27, and 28 are as follows.
(A) The Institute of deposition: NPMD (Location: 2-5-8, Kazusakamatari, Kisarazu-city, Chiba, 292-0818, Japan)
(B) Original depositary date: Oct. 8, 2004
Date of receipt of request for conversion of the original deposits to deposits under the Budapest Treaty (depositary conversion date): May 6, 2005
(C) Accession Nos.:
*Lactobacillus gasseri* OLL2915 strain (Accession No.: NITE BP-25)
*Lactobacillus gasseri* OLL2804 strain (Accession No.: NITE BP-26)
*Lactobacillus gasseri* OLL2818 strain (Accession No.: NITE BP-27)
*Lactobacillus gasseri* OLL2827 strain (Accession No.: NITE BP-28)

The contents for Accession Nos.: NITE BP-145 and 146 are as follows.
(A) The Institute of deposition: NPMD (Location: 2-5-8, Kazusakamatari, Kisarazu-city, Chiba, 292-0818, Japan)
(B) Original depositary date: Oct. 4, 2005
Date of receipt of request for conversion of the original deposits to deposits under the Budapest Treaty (depositary conversion date): Nov. 25, 2005
(C) Accession Nos.:
*Lactobacillus gasseri* OLL2877 strain (Accession No.: NITE BP-145)
*Lactobacillus gasseri* OLL2901 strain (Accession No.: NITE AP-146)

Further, the *Lactobacillus gasseri* deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposits should the depository be unable to furnish a sample when requested, due to the condition of the deposits. During pendency of this application, access to the deposits will be afforded to one determined by the Commissioner to be entitled thereto. All restrictions on the availability to the public of the subject culture deposits will be irrevocably removed upon the granting of a patent disclosing them.

The blood group-specifically-binding lactobacilli *L. gasseri* of the present invention are usable for producing food and drink products compatible with each blood group. The food and drink products produced by using the blood group-specifically-binding lactobacilli *L. gasseri* of the present invention are not restricted in terms of their category and kinds, and may be functional foods, foods for specified health use, health foods, and nursing care foods, or may be confectioneries, lactic acid beverages, dairy products such as cheese and yogurt, seasonings, and such. Forms of the food and drink products are also not restricted, and can be any form of foods and drinks that are usually distributable such as solid-, liquid-, liquid-formula-like-, jelly-like-, tablet-, granule-, or capsule-form. The above-mentioned food and drink products can be produced by usual methods known to those skilled in the art. In the above-mentioned production of food and drink products, one can add sugars, proteins, lipids, dietary fibers, vitamins, trace metals essential for the living body (manganese sulfate, zinc sulfate, magnesium chloride, potassium carbonate, and such), flavorings, and other additives, as long as the growth of lactobacilli is not prevented.

The blood group-specifically-binding lactobacilli *L. gasseri* of the present invention are not only usable when mixed with general foods and drinks but are also usable as starters for the production of, especially, dairy products and fermented milk such as yogurt and cheese. When used as starters, other microorganisms may be mixed in as long as the inhabitation and proliferation of the blood group-specifically-binding lactobacilli *L. gasseri* of the present invention and the production of dairy foods are not adversely affected. For example, *Lactobacillus delbruekii* subsp. *bulgaricus*, *Streptococcus thermophilus*, *Lactobacillus acidophilus*, and such, which are the main bacterial species of lactobacilli for yogurt, can be mixed in and also other bacterial species that are generally used for yogurt and cheese can be mixed in to give starters. Yogurt production using the above-mentioned starters can be carried out by usual methods. For instance, plain yogurt can be produced by mixing the above-mentioned starters with milk or dairy products that have been cooled after being heated, mixed, homogenized, and sterilized, and then fermenting and cooling the mixture.

The food and drink products produced by using the blood group-specifically-binding lactobacilli *L. gasseri* of the present invention comprise the lactobacilli. When a human individual of a compatible ABO blood group consumes the food and drink products, it is expected that the blood group-specifically-binding lactobacilli *L. gasseri* of the present invention contained in the food and drink products will bind to the intestine and proliferate, adjusting and maintaining the intestinal balance and promptly exerting probiotic functions. Thus, the food and drink products are useful not only as general foods and drinks but also as functional foods, health and nutrition foods, nursing care foods, health foods, and such foods used for health-promoting purposes.

The present invention also provides methods of screening for lactobacilli using surface plasmon resonance spectrums. The screening methods of the present invention are for selecting lactobacilli that are compatible with each blood group. The screening methods of the present invention achieve screening by measuring binding ability of lactobacilli to blood group-specific human intestinal mucin and ABO blood group antigens by using surface plasmon resonance spectrums, and carry out the selection using the following points as indicators: (i) having a certain or higher level of binding ability to an ABO blood group antigen of a specific blood group; (ii) not having a certain or higher level of adsorption ability to ABO blood group antigens of blood groups other than the blood group specified in (i) above; and (iii) having a certain or higher level of binding ability to human intestinal mucin of the blood group specified in (i) above. The measurement of binding ability to ABO blood group antigens enables the exclusion of those lactobacilli that mainly bind to sites other than antigens determining blood groups (for example, non-terminal partial structures of sugar chains, sites exposing sialic acids and sulfuric residues, mucin protein portions), and to screen for lactobacilli having a high blood-group specificity. In the present invention, human blood group A-intestinal mucin refers to intestinal mucin derived from ABO blood group A individuals. Similarly, human blood group B-intestinal mucin refers to intestinal mucin derived from blood group B individuals and human blood group O intestinal mucin refers to intestinal mucin derived from blood group O individuals.

In the screening methods of the present invention, an analysis using surface plasmon resonance spectrums is carried out by using ABO blood group antigens and human intestinal mucin as probes. As apparatuses for analyzing interaction among biological molecules using surface plasmon resonance spectrums, one can use, for example, BIACORE1000 (Biacore). The methods for preparing the ABO blood group antigens and human intestinal mucin are as described above. Known immobilization methods are usable to immobilize the probes. The method of immobilization may be by physical adsorption or by adsorption via covalent bonds. To give an example, immobilization can be easily carried out through biotin-avidin binding, by coating chips with streptavidin and biotinylating the probes. Commercially available chips that have been streptavidin-coated (Biacore) may also be used.

As surface plasmon resonance spectrums are used in the methods of the present invention, the above-mentioned "binding ability" is expressed as resonance units (RU). 1 RU indicates that 1 pg of a substance is bound per 1 mm$^2$. In the methods of the present invention, the above-mentioned "certain or higher level of binding ability" is judged using "100 RU" as a criterion. Namely, a judgment that a certain or higher of level/amount lactobacilli are bound to probes is made if a measurement value of "100 RU" or more is obtained. For instance, when a measurement value obtained by using blood group A human-derived intestinal mucin as a probe is 100 RU or more, those lactobacilli are lactobacilli that bind to intestinal mucin. RU values could vary depending on measurement conditions. Temperature conditions of the present methods are, for example, 20 to 40° C., preferably 20 to 30° C., and more preferably 23 to 28° C. Further, preferable sample concentration of the present methods is 0.1 to 0.5 mg/mL, and preferable flow rate of the present methods is 3 to 10 µL/min. As long as the conditions are within the above-mentioned ranges, RU values do not vary even if the above-mentioned conditions are changed; thus one can judge the presence or absence of binding based on "100 RU". Furthermore, even if various conditions such as sample concentrations are changed beyond the above-mentioned ranges, the resulting values are considered to be "100 RU" of the present method as long as the values are substantially equivalent to 100 RU obtained by the above-mentioned conditions. With regard to ability to bind to ABO blood group antigen probes, selection may be made by using values other than "100 RU" if the purpose is to set a stricter selection criterion. In the methods of the present invention, those bacteria with higher RU values are considered to be bacteria that have stronger binding ability to probes (ligands). Thus, one may screen for bacteria that bind to ABO blood group antigen probes at RU values higher than 100 if the purpose is to obtain bacteria having a stronger binding ability. For example, the value may be 150, 200, 300, 400, 500, 600, 700, 800, 900, or 1,000 RU, and as mentioned later in the Examples, one may screen by using 2,000 RU as a criterion. Conversely, with regard to the recognition of undesired blood groups, one may screen by using values stricter than "100 RU or lower" as a criterion. For example, 90, 80, 70, 60, or 50 RU may be used as a criterion.

Meanwhile, when the probes in the screening methods of the present invention are blood group-specific human intestinal mucin, the blood group-specifically-binding lactobacilli are expected to give measurement values (RU) lower than measurement values obtained when ABO blood group probes are used. This is because, when human intestinal mucin is immobilized on a chip, the amount of blood group antigens (sugar chains) bound to the human intestinal mucin is considered to be smaller than the amount obtained when blood group antigens (sugar chains) alone are immobilized on the chip, in terms of an amount per unit area of the chip. With regard to lactobacilli whose measurement values obtained by using a probe for a specific ABO blood group are sufficiently high as compared with values obtained by using a probe for other ABO blood groups, they may qualify as the present invention's blood group-specifically-binding lactobacilli even if measurement values obtained by using as probes human intestinal mucin of that specific blood group are 100 RU or lower, if they can be judged to have utility for the present invention's purposes, by examining whether or not measurement values obtained by using as probes the human intestinal mucin of the specific blood group are sufficiently high as compared with those values obtained by using human intestinal mucin specific for other blood groups. For example, blood group O-compatible lactobacilli can be screened by using as indicators the following points: (i) RU values indicating a binding ability to human ABO blood group A antigens are 100 RU or higher; (ii) RU values indicating binding ability to human ABO blood group B and H antigens are 100 RU or lower; and (iii) RU values indicating a binding ability to blood group A human intestinal mucin are higher than RU values indicating a binding ability to blood group B human intestinal mucin and RU values indicating a binding ability to blood group O human intestinal mucin. Blood group B-compatible lactobacilli can be screened by using as indicators the following points: (i) RU values indicating a binding ability to human ABO blood group B antigens are 100 RU or higher; (ii) the RU values indicating binding ability to human ABO blood group A and H antigens are 100 RU or lower; and (iii) RU values indicating a binding ability to blood group B human intestinal mucin are higher than RU values indicating a binding ability to blood group A human intestinal mucin and RU values indicating a binding ability to blood group O human intestinal mucin. As for blood group O-compatible lactobacilli, screening is possible by using as indicators the following points: (i) RU values indicating a binding ability to human ABO blood group H antigens are 100 RU or higher; (ii) RU values indicating binding ability to human ABO blood group A and B antigens are 100 RU or lower; and (iii) RU values indicating a binding ability to blood group O human intestinal mucin are higher than RU values indicating a binding ability to blood group A human intestinal mucin and RU values indicating a binding ability to blood group B human intestinal mucin.

In surface plasmon resonance spectrum measurement, RU values may sometime become abnormally high due to bacterial aggregation caused by non-specific adsorption of test bacteria. As a result of this, adsorption to human-derived intestinal mucin or ABO blood group antigens may not be correctly reflected on measurement results. Thus, if abnormally high values are obtained, the lactobacilli under examination can be eliminated from screening because non-specific adsorption (bacterial aggregation) is suspected.

Targets of the present invention's screening methods are not especially restricted, as long as they are lactobacilli. If examples of targets were to be cited, preferably used are *Lactobacillus acidophilus, Lactobacillus crispatus, Lactobacillus amylovorus, Lactobacillus gallinarum, Lactobacillus gasseri, Lactobacillus johnsonii, Lactobacillus casei, Lactobacillus rhamnosus, Lactobacillus zeae, Lactobacillus reuteri, Lactobacillus delbruekii* subsp. *bulgaricus, Lactobacillus delbruekii* subsp. *lactis, Lactobacillus fermentum, Lactobacillus murinus, Bifidobacterium animalis, Bifidobacterium bifidum, Bifidobacterium breve, Bifidobacterium infantis, Bifidobacterium longum, Bifidobacterium pseudolongum, Enterococcus faecium, Enterococcus fecalis,* and *Streptococcus thermophilus*. More preferable target examples are genus *Lactobacillus*, and the most preferable target examples are lactobacilli of *Lactobacillus acidophilus* group, which include *L. gasseri*.

The lactobacilli screened by the methods of the present invention are those lactobacilli that are highly likely to bind to human intestine of a specified ABO blood group. Individuals of the specified blood group can promote health by taking in lactobacilli screened by the methods of the present invention, thanks to effects such as improvement of intestinal balance in a short period of time. Therefore, lactobacilli screened by the methods of the present invention are applicable to food and drink products, functional foods, foods for specified health use, dairy products, lactic acid bacteria beverages, and such for human individuals of a specified blood group.

All prior art references cited in the present specification are incorporated herein by reference.

EXAMPLES

Herein below, the present invention will be specifically explained based on examples, but it is not to be construed as being limited thereto.

Example 1

Gas Production Test

Lactobacilli that do not produce gas are preferred as lactobacilli used in yogurt production. This is because Japanese law requires selling yogurt in airtight containers. This also prevents product defects and ruptures due to container expansion accompanying gas production. Thus, gas production tests were carried out with 238 strains.

A lactobacilli activation culture (37° C., 18 hours) was carried out twice in MRS Broth (DIFCO). Aluminum-capped test tubes each containing a Durham tube and MRS Broth (5 mL) were sterilized (121° C., 15 minutes). Durham tubes were put into the tubes with their openings at the bottom and air bubbles were removed from the Durham tubes during sterilization. 10 μL of *lactobacillus* suspension at about $10^9$ cfu/mL was inoculated into each of the above-mentioned sterilized aluminum-capped test tubes and cultured anaerobically at 37° C. for 24 hours. After the end of the culture, presence or absence of gas accumulated in Durham tubes was visually observed. When presence of obvious air bubbles was observed, the sample was judged as gas-production positive (+) (Table 1).

Example 2

Analysis of Blood Group Antigen-Recognizing Ability

To obtain lactobacilli for blood group-compatible yogurt, the present inventors decided to select lactobacilli that recognize and bind to blood group antigens by using surface plasmon resonance spectrums. As test sample bacteria, 238 strains belonging to the *Lactobacillus acidophilus* group (*L. gasseri, L. plantarum, L. crispatus, L. amylovorus, L. casei, L. salivarius, L. brevis, L. fermentum*, and such) were prepared. BIACORE1000 was used as the apparatus for surface plasmon resonance spectrum analysis.

2-(1) Preparation of Analytes

Each bacterial strain was seeded to start culture and passaged three times in an MRS medium, and then cultured for 12 hours and dispensed into 1.5 mL volume tubes in 500 μL aliquots. Bacteria obtained by centrifugal separation of these suspensions (6,000 rpm at 4° C. for 10 minutes) were washed twice in PBS (pH 7.2), freeze-dried, and suspended at a concentration of 0.1 mg/mL by using HBS-EP buffer (0.01 M HEPES, pH 7.4, 0.15 M NaCl, 3 mM EDTA, 0.005% Surfactant P20) to give an analyte suspension.

2-(2) Blood Group Antigen Probes and their Immobilization onto Chips

Antigenic structures of human ABO blood group substances were used as probes for selecting bacteria. Specifically, the following biotinylated polymer probes of trisaccharide sugar chains (Seikagaku Corporation) (herein below, also described as "BP-probe(s)") were used:

A antigen probe: [GalNAcα1-3(Fucα1-2)Gal-]
B antigen probe: [Galα1-3(Fucα1-2)Gal-]
H antigen probe: [Fucα1-2Gal-]

Figure 2:
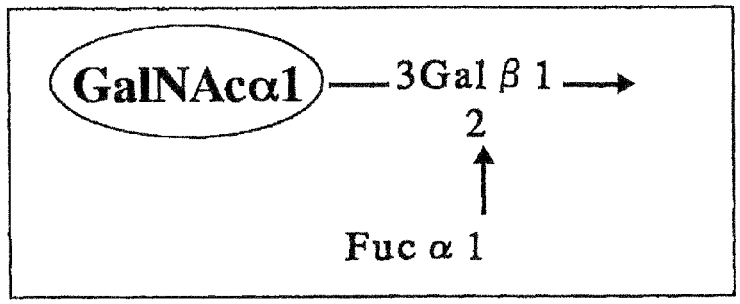
FIG. 2 is a drawing showing the sugar chain portion of a blood group A antigen BP probe (top), the sugar chain portion of a blood group B antigen BP probe (middle), and the sugar chain portion of a blood group O antigen BP probe (bottom).
Figure 2:
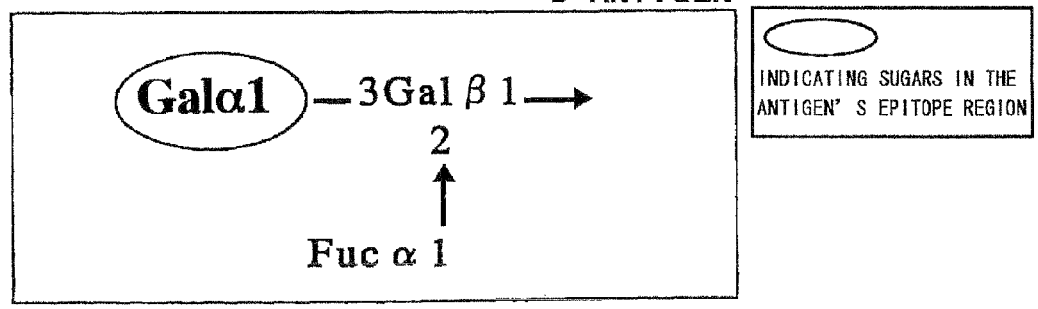
Figure 2:
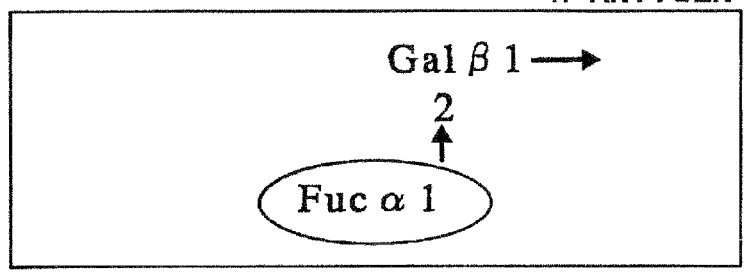

With regard to the above-mentioned BP probes, chemical structures are depicted in FIG. 1 and sugar chain structures are depicted in FIG. 2.

The above-mentioned blood group antigen BP probes were prepared at 0.1 mg/10 mL with HBS-EP buffer (pH 7.4). This solution was added to Sensor Chip SA (Biacore) and the commercialized probes were immobilized onto the sensor chip surface via biotin-avidin reaction. Sensor Chip SA is a chip with immobilized streptavidin for exclusive use of BIACORE. The amount of immobilized A antigen probe was set to an amount that gives 750 RU, and the amount of immobilized B antigen probe was set to an amount that gives 850 RU. Immobilization of O antigen probes was carried out as follows: a reaction was carried out in an acetic acid buffer at pH 4.5, at 55° C., for 20 hours by treating 1 mg of A antigen sugar chain probes (Seikagaku Corporation) with 0.5 U of the enzyme α-N-acetylgalactosaminidase (E.C.3.2.1.97, *Streptococcus pneumoniae*-derived, SIGMA, JAPAN) that hydrolyzes GalNAc existing as an α-linkage, thereby removing the terminal GalNAc of the probes (a removal ratio measurement using A antigen antibodies continued that 80% or more of GalNAc was removed). The biotinylated group H antigen sugar chain probes were immobilized onto avidin-bound sensor chips in a similar manner with group A antigen sugar chain probes. The binding amount in this case was about 1,000 RU.

2-(3) Preparation of Human Intestinal Mucin and their Immobilization onto Chips

Human colonic mucin was prepared as the other ligand for bacteria selection. Blood group A human intestine (the colon), blood group B human intestine (the colon), and blood group O human intestine (the colon) were acquired from the Tohoku University Graduate School of Medicine as subdivided test sample specimens. Mucus mucin layers were collected from normal parts of the colons by scraping the surface. The mucin layers were defatted by using Folch's solvent and diethyl ether and dried, followed by an extraction with a 4 M guanidine hydrochloride solution at 37° C. for two hours. Gel filtration was carried out and the obtained filtrates were used for tests as purified human blood group A, B, or O intestinal mucin (human colonic mucin: HCM, herein below, blood group A, B, and O intestinal mucin are sometimes abbreviated as A-HCM, B-HCM, and O-HCM, respectively). Purification by gel filtration was carried out according to the human colonic mucin purification method described in "Purushothaman, S. S. et al, Adherence of *Shigella dysenteriae* 1 to Human Colonic Mucin. Curr. Microbiol., 42(6), 381-387 (2001)". 4M guanidine hydrochloride solution was used as mobile phase and a Toyopearl HW-65F column (90 cm×2.6 cm, Tosoh, Tokyo, Japan) was used. With regard to the detection, neutral sugars and proteins were measured by a phenol-sulfuric acid method (490 nm) and by absorbance at 280 nm, respectively. Fractions with protein absorbance and highest neutral sugar content peaks were selected. These were further fractionated based on a molecular weight of about 2,000,000 or more and were isolated as human colonic mucin (HCM) preparations. The obtained HCMs were confirmed for human blood group substrate antigenicity of each blood group by using antibodies, The sampling of the above-mentioned specimens was carried out with the approval of the Ethical Committee of the Tohoku University Graduate School of Medicine, and the consent of patients.

Immobilization of HCMs to chips for BIACORE1000 was carried out by an amine coupling method. First, a mixed reagent solution consisting of 50 μL of 75.0 mg/mL N-ethyl-N'-(3-dimethyl aminopropyl-carbodiimide hydrochloride) (EDC) and 50 μL of 11.5 mg/mL N-hydroxysuccinimide (NHS) was run over the sensor chip CM5 to which a carboxymethyl dextran group has been introduced in advance, and thereby the carboxyl groups introduced at the dextran termini were activated. A mixed solution of 120 μL of acetic acid buffer (pH 4.0) for immobilization and 30 μL of HCM-A was run over them, and the HCM was covalently bound thereto through an amine coupling reaction. Next, remaining active groups at sites where no ligands were bound were blocked by using a 1M ethanolamine hydrochloride-NaOH solution (pH 8.5). HBS-EP buffer was used as running buffer. The amount of immobilized HCM was set to 1,000 to 2,000 RU so that the screening methods of the present invention can be conducted in a highly reproducible manner.

2-(4) Measurement by BIACORE1000

An interaction of the above-mentioned analytes with blood group antigens was analyzed with BIACORE1000 by using the above-mentioned chips with immobilized blood group antigen probes or chips with immobilized HCM. The BIACORE1000 measurement conditions are shown below:

Running buffer solution: HBS-EP buffer (pH 7.4)
Loaded sample volume: 20 μL
Flow rate: 3 μL/min
Temperature: 25° C.
Regeneration solution: 5 μL of 1 M guanidine hydrochloride solution In BIACORE analyses, the interaction between analytes and blood group antigens is expressed by resonance units (RU). One resonance unit indicates the binding of 1 pg substance per 1 $mm^2$. Results are shown in Table 1.

| | Selection of blood group A-compatible lactobacilli | | | | | | | | | |
|---|---|---|---|---|---|---|---|---|---|---|
| Bacterial strains | A antigen-recognizing ability (RU) | Gas production | B antigen-recognizing ability (RU) | A antigen-recognizing ability/ B antigen-recognizing ability | H antigen-recognizing ability (RU) | A antigen-recognizing ability/ H antigen-recognizing ability | A-HCM-recognizing ability (RU) | O-HCM-recognizing ability (RU) | Bile-acid tolerance ($OD_{650}$) | Stomach-acid tolerance (Survival rate %) |
| MEP 165501 | 0.0 | − | 6.5 | 0.0 | 956.6 | 0.0 | 0.0 | 0.0 | 0.112 | 0.003 |
| MEP 165502 | 0.0 | − | 716.7 | 0.0 | 997.2 | 0.0 | 0.0 | 48.0 | 0.135 | 0.874 |
| MEP 165503 | 0.0 | − | 0.0 | ∞ | 931.1 | 0.0 | 0.0 | 87.0 | 0.224 | 1.798 |
| *L. gasseri* OLL 2804 | 2086.3 | − | 28.6 | 72.9 | 5.1 | 409.1 | 829.2 | 0.0 | 0.119 | 24.906 |
| *L. gasseri* OLL 2818 | 3981.3 | − | 52.3 | 76.1 | 18.7 | 212.9 | 598.2 | 0.0 | 0.117 | 6.212 |

| | Selection of blood group O-compatable lactobacilli | | | | | | | | | |
|---|---|---|---|---|---|---|---|---|---|---|
| Bacterial strains | H antigen-recognizing ability (RU) | Gas production | A antigen-recognizing ability (RU) | H antigen-recognizing ability/ A antigen-recognizing ability | B antigen-recognizing ability (RU) | H antigen-recognizing ability/ B antigen-recognizing ability | O-HCM-recognizing ability (RU) | A-HCM-recognizing ability (RU) | Bile-acid tolerance ($OD_{650}$) | Stomach-acid tolerance (Survival rate %) |
| MEP 165504 | 14.8 | + | 7957.2 | 0.0 | 3.9 | 3.8 | 38.0 | 101.4 | 1.310 | 0.003 |
| MEP 165505 | 0.0 | − | 2415.2 | 0.0 | 40.2 | 0.0 | 0.0 | 539.6 | 1.164 | 0.000 |
| MEP 165506 | 5.3 | − | 2336.3 | 0.0 | 12.5 | 0.4 | 0.0 | 51.3 | 0.135 | 0.851 |
| *L. gasseri* OLL 2827 | 25761.8 | − | 32.0 | 805.1 | 47.4 | 543.5 | 509.0 | 893.5 | 0.118 | 0.959 |
| *L. gasseri* OLL 2915 | 1061.7 | − | 0.0 | ∞ | 10.9 | 97.4 | 6233.0 | 665.7 | 0.086 | 0.585 |

Selection of blood group B-compatable lactobacilli

| Bacterial strains | B antigen-recognizing ability (RU) | Gas production | A antigen-recognizing ability (RU) | B antigen-recognizing ability/ A antigen-recognizing ability | H antigen-recognizing ability (RU) | B antigen-recognizing ability/ H antigen-recognizing ability |
|---|---|---|---|---|---|---|
| MEP 165507 | 0 | − | 224.8 | 0.0 | 0 | 0.0 |
| MEP 165508 | 0 | + | 0 | 0.0 | 96.1 | 0.0 |
| MEP 165509 | 0 | − | 0 | 0.0 | 0 | 0.0 |
| L. gasseri OLL 2877 | 4220.9 | − | 66.4 | 63.6 | 0 | ∞ |
| L. gasseri OLL 2901 | 2000.9 | − | 0 | ∞ | 0 | ∞ |

Selection of blood group B-compatable lactobacilli

| Bacterial strains | B-HCM-recognizing ability (RU) | A-HCM-recognizing ability (RU) | O-HCM-recognizing ability (RU) | Bile-acid tolerance ($OD_{650}$) | Stomach-acid tolerance (Survival rate %) |
|---|---|---|---|---|---|
| MEP 165507 | 0.0 | 0.0 | 2.4 | 0.339 | 0.011 |
| MEP 165508 | 18.7 | 0.0 | 531.4 | 2.020 | 0.010 |
| MEP 165509 | 0.0 | 0.0 | 154.0 | 0.000 | 1.499 |
| L. gasseri OLL 2877 | 1406.3 | 218.2 | 0.0 | 0.651 | 10.812 |
| L. gasseri OLL 2901 | 17.1 | 0.0 | 7.6 | 0.031 | 8.923 |

2-(5) Selection of Bacteria (Part 1)

Lactobacilli were selected according to the results obtained above. First, selection was carried out according to the above-mentioned BIACORE1000 measurement results and the results of gas-production test of Example 1.

Lactobacilli for yogurt for blood group A were selected based on (i) group A antigen-recognizing ability and (ii) gas production. The selection criteria were:

(i) blood group A antigen-recognizing ability: results obtained by BIACORE1000 measurement using blood group A antigen probes were 2,000 RU or higher (within about top 35%).

(ii) gas production: the gas production test showed no gas production (−).

By this process, the 238 *lactobacillus* strains were narrowed down to 43 strains.

Similarly, lactobacilli for yogurt for blood group O were selected based on (i) blood group H antigen-recognizing ability and (ii) gas production. The selection criteria were:

(i) blood group H antigen-recognizing ability: results obtained by BIACORE 1000 measurement using group H antigen probes were 700 RU or higher (within about top 13%).

(ii) gas production: the gas production test showed no gas production (−).

By this process, the 238 *lactobacillus* strains were narrowed down to 14 strains.

Similarly, lactobacilli for yogurt for blood group B were selected based on (i) blood group B antigen-recognizing ability and (ii) gas production. The selection criteria were:

(i) blood group B antigen-recognizing ability: the results obtained by BIACORE1000 measurement using group B antigen probes were 2,000 RU or higher (within about top 14%).

(ii) gas production: gas production was not seen by the gas production test (−).

By this process, the 238 *lactobacillus* strains were narrowed down to 25 strains.

2-(6) Selection of Bacteria (Part 2)

As mentioned above, 43 *lactobacillus* strains were selected as *lactobacillus* candidates for yogurt for blood group A. These strains recognize blood group A antigens and produce no gas. Of these, the candidates were further selected based on (i) the absence of recognizing ability for other blood group antigens (B antigens and H antigens) and (ii) the specific recognition of A antigens. Selection criteria were:

(i) recognizing ability for other blood group antigens (B antigens and H antigens)

B antigen-recognizing ability: results obtained by BIACORE1000 measurement using B-antigen probes were 100 RU or lower, H antigen-recognizing ability: results obtained by BIACORE1000 measurement using H antigen probes were 100 RU or lower, (ii) Specific recognizing ability for A antigens The ratio of A antigen-recognizing ability/B antigen-recognizing ability was 70 or higher, and the ratio of A antigen-recognizing ability/H antigen-recognizing ability was 100 or higher.

By this process, 13 strains were selected from the 43 strains.

Similarly, *lactobacillus* candidates for yogurt for blood group O were also selected. The section criteria were:

(i) recognizing ability for other blood group antigens (A antigens and B antigens)

A antigen-recognizing ability: the results obtained by BIACORE1000 measurement using A antigen probes were 100 RU or lower, B antigen-recognizing ability: the results obtained by BIACORE1000 measurement using B antigen probes were 100 RU or lower, (ii) Specific recognizing ability for H antigens The ratio of H antigen-recognizing ability/A antigen-recognizing ability was 800 or higher, and the ratio of H antigen-recognizing ability/B antigen-recognizing ability was 20 or higher. By this process, five strains were selected from the 14 strains.

Similarly, *lactobacillus* candidates for yogurt for blood group B were also selected. The section criteria were:
(i) recognizing ability for other blood group antigens (A antigens and H antigens)
A antigen-recognizing ability: results obtained by BIACORE1000 measurement using A antigen probes were 100 RU or lower,
H antigen-recognizing ability: results obtained by BIACORE1000 measurement using H antigen probes were 100 RU or lower,
(ii) Specific recognizing ability for B antigens
The ratio of B antigen-recognizing ability/A antigen-recognizing ability was 50 or higher, and the ratio of B antigen-recognizing ability/H antigen-recognizing ability was 50 or higher. By this process, 6 strains were selected from the 25 strains.

2-(7) Selection of Bacteria (Part 3)

The bacterial strains selected above were further selected according to the recognizing ability for blood group-specific human colonic mucin (HCM).

From the *lactobacillus* candidates for yogurt for blood group A, (i) those recognizing A-HCM were selected and (ii) those recognizing O-HCM were eliminated. Specifically, selection criteria were: (i) having 100 RU or higher A-HCM-recognizing ability and (ii) having 100 RU or lower O-HCM-recognizing ability, both from BIACORE1000 measurement results using human HCM. Further, MEP165511 strain and MEP165530 strain showed recognizing ability at 10,000 RU or higher and were eliminated on suspicion of bacterial aggregation. According to the above selections, two *bacillus* strains (*L. gasseri* OLL 2804 and *L. gasseri* OLL 2818) were selected from the 13 strains.

Similarly, from the *lactobacillus* candidates for yogurt for blood group 0, (i) those recognizing O-HCM were selected and (ii) those with a relatively high recognizing ability of A-HCM were eliminated. Namely, selection criteria were: (i) having 100 RU or higher O-HCM-recognizing ability and (ii) having 1,000 RU or lower A-HCM-recognizing ability in BIACORE1000 measurement results using human HCM. According to the above-mentioned selections, two *bacillus* strains (*L. gasseri* OLL 2827 and *L. gasseri* OLL 2915) were selected from the five strains.

Similarly, with the *lactobacillus* candidates for yogurt for blood group B, the selection criterion was that the B-HCM-recognizing ability is higher than A-HCM- and H-HCM-recognizing abilities. According to the above-mentioned selections, two *bacillus* strains (*L. gasseri* OLL 2877 and *L. gasseri* OLL 2901) were selected from six strains.

Example 3

Stomach-Acid Tolerance Test and Bile-Acid Tolerance Test

Lactobacilli incorporated into a body in the form of yogurt preferably stay alive in the intestine to fully exert their functions. For this reason, stomach-acid tolerance test and bile-acid tolerance test were carried out.

3-(1) Stomach-Acid Tolerance Test

One milliliter bacterial suspension of lactobacilli, prepared by two activation cultures (37° C., 18 hours) in Lactobacilli MRS broth (DIFCO) followed by two washes with physiological saline, was added to 9 mL of filter-sterilized artificial stomach acid at pH 2 [NaCl (0.2%), pepsin (1:5000, Tokyo Chemical Industry Co., Ltd) (0.35%): adjusted to pH 2 with 1N hydrochloric acid], and kept in contact for two hours under aerobic conditions. After this, 1 mL aliquot was taken from the mixture, and the reaction was stopped by adding 9 mL of 67 mM phosphate buffer (pH 6.5). Numbers of live bacteria before and after the contact with the artificial stomach acid were measured by using Lactobacilli MRS Agar (DIFCO) to calculate viability (%).

The selection criterion, although varying depending on bacterial species, was set to 0.5 or more, because all the bacilli selected in the present case were *Lactobacillus gasseri*. All of lactobacilli for blood-group A yogurt (*L. gasseri* OLL 2804 and *L. gasseri* OLL 2818), for blood-group O yogurt (*L. gasseri* OLL 2827 and *L. gasseri* OLL 2915), and for blood group B yogurt (*L. gasseri* OLL 2877 and *L. gasseri* OLL 2901), fulfilled the above criterion (Table 1).

3-(2) Bile-Acid Tolerance Test

Ten micro litters of lactobacilli prepared by two activation cultures in Lactobacilli MRS broth (DIFCO) (37° C., 18 hours) was inoculated to 5 mL of Lactobacilli MRS broth (DIFCO) containing 0.9% Bacto-Oxgall (DIFCO), and then anaerobically cultured at 37° C. At 18 hours after the culture, medium turbidity ($OD_{650}$) was measured.

The selection criterion, although varying depending on bacterial species, was set to 0.08 or more with lactobacilli for blood-group A yogurt and lactobacilli for blood-group O yogurt. Both of lactobacilli for blood-group A yogurt (*L. gasseri* OLL 2804 and *L. gasseri* OLL 2818) and lactobacilli for blood-group O yogurt (*L. gasseri* OLL 2827 and *L. gasseri* OLL 2915) fulfilled the above criterion (Table 1). Among lactobacilli for blood-group B yogurt, the bile-acid tolerance of *L. gasseri* OLL2901 was 0.031, but this is considered to be within a range that causes no special problem regarding retention in the intestine. Scientific properties of the above-described six *bacillus* strains are shown in Table 2.

TABLE 2

| | Blood Group A | | Blood Group O | | Blood Group B | |
|---|---|---|---|---|---|---|
| | 2804 Strain | 2818 Strain | 2827 Strain | 2915 Strain | 2877 Strain | 2901 Strain |
| Features of colonies on medium (*Lactobacillus* MRS Ager, DIFCO) | Round shape Light yellow Smooth Flat | Round shape Light yellow Smooth Flat | Round shape Light yellow Smooth Flat | Round shape Light yellow Smooth Flat | Round shape Light yellow Smooth Flat | Round shape Light yellow Smooth Flat |
| Bacterial shape | Bacilliform | Bacilliform | Bacilliform | Bacilliform | Bacilliform | Bacilliform |
| Gram stain | Positive | Positive | Positive | Positive | Positive | Positive |
| Type of lactate fermentation | Homolactic fermentation | Homolactic fermentation | Homolactic fermentation | Homolactic fermentation | Homolactic fermentation | Homolactic fermentation |
| Aerobic growth | + | + | + | + | + | + |

TABLE 2-continued

|  |  | Blood Group A | | Blood Group O | | Blood Group B | |
| --- | --- | --- | --- | --- | --- | --- | --- |
|  |  | 2804 Strain | 2818 Strain | 2827 Strain | 2915 Strain | 2877 Strain | 2901 Strain |
| Temperature for growth |  | 15° C.–45° C.+ | 15° C.–45° C.+ | 15° C.–45° C.+ | 15° C.–45° C.+ | 15° C.–45° C.+ | 15° C.–45° C.+ |
| Sugar fermentability | Arabinose | – | – | – | – | – | – |
|  | Xylose | – | – | – | – | – | – |
|  | Rhamnose | – | – | – | – | – | – |
|  | Ribose | – | – | – | – | – | – |
|  | Glucose | + | + | + | + | + | + |
|  | Mannose | + | + | + | + | + | + |
|  | Fructose | + | + | + | + | + | + |
|  | Galactose | + | + | + | + | + | + |
|  | Sucrose | + | + | + | + | + | + |
|  | Cellobiose | + | + | + | + | + | + |
|  | Lactose | + | – | + | – | – | + |
|  | Trehalose | + | + | + | + | + | + |
|  | Melibiose | + | – | – | – | – | – |
|  | Raffinose | – | – | – | – | – | – |
|  | Melezitose | – | – | – | – | – | – |
|  | Mannitol | – | – | – | – | – | – |
|  | Sorbitol | + | – | – | – | – | – |
| Gas production |  | – | – | – | – | – | – |
| Stomach-acid tolerance (survival rate, %) |  | 24.906 | 6.212 | 0.959 | 0.585 | 10.812 | 8.923 |
| Bile-acid tolerance ($OD_{650}$) |  | 0.119 | 0.117 | 0.118 | 0.086 | 0.651 | 0.031 |

Example 4

Production of Yogurt Using Blood Group-Specifically-Binding Lactobacilli

Yogurt was produced by using the lactobacilli (lactobacilli for yogurt for blood group A: *L. gasseri* OLL 2804 and *L. gasseri* OLL 2818, lactobacilli for yogurt for blood group O: *L. gasseri* OLL 2827 and *L. gasseri* OLL 2915) selected as mentioned above.

4-(1) An Example of Yogurt Production Using *L. gasseri* OLL 12804

Plain yogurt was prepared by using *L. gasseri* OLL 2804 strain. First, bulk starters were prepared by inoculating *L. gasseri* OLL 2804 strain, *L. bulgaricus* JCM $1002^T$, and *S. thermophilus* ATCC 19258 at 1% each to 10% nonfat-dry-milk media and culturing them at 37° C. for 15 hours.

The starters of *L. bulgaricus* JCM $1002^T$ and *S. thermophilus* ATCC 19258 were inoculated at 1% each and the starter of *L. gasseri* OLL 2804 strain was inoculated at 5% to a yogurt mix (SNF: 9.5%, FAT: 3.0%) that had been heat-treated at 95° C. for five minutes, and fermentation was carried out at 43° C. for four hours.

Numbers of live *L. gasseri* OLL 2804, *L. bulgaricus* JCM $1002^T$, and *S. thermophilus* ATCC 19258, immediately after fermentation and cooling, were $12.5 \times 10^7$ CFU/mL, $14.0 \times 10^7$ CFU/mL, and $11.8 \times 10^8$ CFU/mL, respectively, and both the flavor and physical properties were good. When the above-mentioned yogurt was preserved at 10° C., numbers of live bacilli on day 25 of preservation were $9.60 \times 10^7$ CFU/mL for *L. gasseri* OLL 2804, $7.50 \times 10^7$ CFU/mL for *L. bulgaricus* JCM $1002^T$, and $11.0 \times 10^7$ CFU/mL for *S. thermophilus* ATCC 19258. The decrease in live *L. gasseri* OLL 2804 number was small as shown by its survival rate being 77% of the live *bacillus* number on day 1 of the preservation. Flavor and physical properties of the preserved product were also good.

4-(2) An Example of Yogurt Production Using *L. gasseri* OLL 2818

Plain yogurt was prepared by using *L. gasseri* OLL 2818 strain. First, bulk starters were prepared by inoculating *L. gasseri* OLL 2818 strain, *L. bulgaricus* JCM $1002^T$, and *S. thermophilus* ATCC 19258 at 1% each to 10% nonfat-dry-milk media and culturing them at 37° C. for 15 hours.

The starters of *L. bulgaricus* JCM $1002^T$ and *S. thermophilus* ATCC 19258 were inoculated at 1% each and the starter of *L. gasseri* OLL 2818 strain was inoculated at 5% to a yogurt mix (SNF: 9.5%. FAT: 3.0%) that had been heat-treated at 95° C. for five minutes, and fermentation was carried out at 43° C. for four hours.

Numbers of live *L. gasseri* OLL 2818, *L. bulgaricus* JCM $1002^T$, and *S. thermophilus* ATCC 19258, immediately after fermentation and cooling, were $14.0 \times 10^7$ CFU/mL, $20.0 \times 10^7$ CFU/mL, and $11.4 \times 10^8$ CFU/mL, respectively, and both the flavor and physical properties were good. When this yogurt was preserved at 10° C., numbers of live bacilli on day 25 of preservation were $11.4 \times 10^7$ CFU/mL for *L. gasseri* OLL 2818, $7.00 \times 10^7$ CFU/mL for *L. bulgaricus* JCM $1002^T$, and $10.0 \times 10^7$ CFU/mL for *S. thermophilus* ATCC 19258. The decrease in live *L. gasseri* OLL 2818 number was small as shown by the survival rate being 82% of the live *bacillus* number on day 1 of preservation. The flavor and physical properties of the preserved product were also good.

INDUSTRIAL APPLICABILITY

The present invention provides human ABO blood group-compatible lactobacilli and methods for screening them. The lactobacilli of the present invention or the *lactobacillus* strains obtained by the screening methods of the present invention are lactobacilli that have a high ability to bind to the intestine of each of the ABO-blood groups. By applying these lactobacilli to the production of food and drink products, it becomes possible to provide new probiotic food and drink products, including yogurt with blood group-specific functions.

We claim:

1. A method of screening for a human blood group A-compatible *lactobacillus*, comprising:
   (a) providing a candidate *lactobacillus*;
   (b) determining ability of the candidate *lactobacillus* to recognize a human blood group A antigen, a human blood group B antigen, and a human blood group H antigen, wherein the recognizing ability is determined by measuring response units (RU) of surface plasmon resonance spectrum, wherein the human blood group A antigen comprises [GalNAcα1-3(Fucα1-2)Gal-]; and
   (c) selecting the candidate *lactobacillus* as a human blood group A-compatible *lactobacillus* if:
      (i) blood group A antigen-recognizing ability is 2,000 RU or higher;
      (ii) blood group B antigen-recognizing ability is 100 RU or lower;
      (iii) blood group H antigen-recognizing ability is 100 RU or lower;
      (iv) ratio of the blood group A antigen-recognizing ability to the blood group B antigen-recognizing ability is 70 or higher;
      (v) ratio of the blood group A antigen-recognizing ability to the blood group H antigen-recognizing ability is 100 or higher;
      (vi) A-HCM-recognizing ability is 100 RU or higher; and
      (vii) O-HCM-recognizing ability is 100 RU or lower.

2. The method, according to claim 1, wherein the human blood group B antigen comprises [Galα1-3 (Fucα1-2)Gal-].

3. The method, according to claim 1, wherein the human blood group H antigen comprises [Fucα1-2Gal-].

4. A method of screening for a human blood group B-compatible *lactobacillus*, comprising:
   (a) providing a candidate *lactobacillus*;
   (b) determining ability of the candidate *lactobacillus* to recognize a human blood group A antigen, a human blood group B antigen, and a human blood group H antigen using surface plasmon resonance, wherein the recognizing ability is determined by measuring response units (RU) of surface plasmon resonance spectrum, wherein the human blood group B antigen comprises [Galα1-3(Fucα1-2)Gal-]; and
   (c) selecting the candidate *lactobacillus* as a human blood group B-compatible *lactobacillus* if:
      (i) blood group B antigen-recognizing ability is 2,000 RU or higher;
      (ii) blood group A antigen-recognizing ability is 100 RU or lower;
      (iii) blood group H antigen-recognizing ability is 100 RU or lower;
      (iv) ratio of the blood group B antigen-recognizing ability to the blood group A antigen-recognizing ability is 50 or higher;
      (v) ratio of the blood group B antigen-recognizing ability to the blood group H antigen-recognizing ability is 20 or higher; and
      (vi) B-HCM-recognizing ability is higher than A-HCM-recognizing ability and O-HCM recognizing ability.

5. The method, according to claim 4, wherein the human blood group A antigen comprises [GalNAcα1-3(Fucα1-2)Gal-].

6. The method, according to claim 4, wherein the human blood group H antigen comprises [Fucα1-2Gal-].

7. A method of screening for a human blood group O-compatible *lactobacillus*, comprising:
   (a) providing a candidate *lactobacillus*;
   (b) determining ability of the candidate *lactobacillus* to recognize a human blood group A antigen, a human group B antigen, and a human group H antigen using surface plasmon resonance, wherein the recognizing ability is determined by measuring response units (RU) of surface plasmon resonance spectrum, wherein the human blood group H antigen comprises [Fucα1-2Gal-]; and
   (c) selecting the candidate *lactobacillus* as a human blood group O-compatible *lactobacillus* if:
      (i) blood group H antigen-recognizing ability is 700 RU or higher;
      (ii) blood group A antigen-recognizing ability is 100 RU or lower;
      (iii) blood group B antigen-recognizing ability is 100 RU or lower;
      (iv) ratio of the blood group H antien-recognizing ability to the blood group A antigen-recognizing ability is 800 or higher;
      (v) ratio of the blood group H antigen-recognizing ability to the blood group B antigen-recognizing ability is 20 or higher;
      (vi) O-HCM-recognizing ability is 100 RU or higher; and
      (vii) A-HCM-recognizing ability is 1,000 RU or lower.

8. The method, according to claim 7, wherein the human blood group A antigen comprises [GalNAcα1-3(Fucα1-2)Gal-].

9. The method, according to claim 7, wherein the human blood group B antigen comprises [Galα1-3(Fucα1-2)Gal-].

* * * * *